US00PP25966P3

(12) United States Plant Patent
Hooper

(10) Patent No.: US PP25,966 P3
(45) Date of Patent: Sep. 29, 2015

(54) ***AGAPANTHUS* PLANT NAMED 'BRILLIANT BLUE'**

(50) Latin Name: *Agapanthus hybrida*
Varietal Denomination: Brilliant Blue

(71) Applicant: Vance James Hooper, Waitara (NZ)

(72) Inventor: Vance James Hooper, Waitara (NZ)

( * ) Notice: Subject to any disclaimer, the term of this patent is extended or adjusted under 35 U.S.C. 154(b) by 43 days.

(21) Appl. No.: 13/999,297

(22) Filed: Feb. 7, 2014

(65) Prior Publication Data

US 2015/0230384 P1 Aug. 13, 2015

(51) Int. Cl.
*A01H 5/02* (2006.01)

(52) U.S. Cl.
USPC ..... Plt./398

(58) Field of Classification Search
USPC ..... Plt./398
CPC ..... A01H 5/02
See application file for complete search history.

*Primary Examiner* — Kent L Bell

(57) ABSTRACT

A new cultivar of *Agapanthus* plant named 'Brilliant Blue' that is characterized by flowers having dark blue petals with a darker blue center stripe, a compact dwarf habit, a long flowering season, short peduncles and short pedicels.

1 Drawing Sheet

Botanical classification: *Agapanthus hybrida.*
Variety denomination: 'Brilliant Blue'.

BACKGROUND OF THE INVENTION

The present invention relates to a new and distinct cultivar of *Agapanthus* plant botanically known as *Agapanthus hybrida* and hereinafter referred to by the cultivar name 'Brilliant Blue'.

'Brilliant Blue' originated from open pollination of the female or seed parent plant *Agapanthus campanulatus* 'Lapis' (not patented). The male or pollen parent plant is unknown. The resulting seeds were subsequently harvested and grown. 'Brilliant Blue' was selected as a single plant from within the stated progeny in a controlled environment in Waitara, New Zealand in 2002.

Asexual reproduction of the new cultivar 'Brilliant Blue' first occurred by division in 2005 in Waitara, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Agapanthus* cultivar 'Brilliant Blue'. These traits in combination distinguish 'Brilliant Blue' as a new and distinct cultivar apart from other existing known varieties of *Agapanthus.*

1. *Agapanthus* 'Brilliant Blue' exhibits a large number of flowers having dark blue petals with a darker blue center stripe.
2. *Agapanthus* 'Brilliant Blue' exhibits a compact dwarf habit.
3. *Agapanthus* 'Brilliant Blue' exhibits a long flowering season.
4. *Agapanthus* 'Brilliant Blue' exhibits short peduncles and pedicels.

The closest comparison cultivar is the female or seed parent plant *Agapanthus* 'Lapis' (not patented).

'Brilliant Blue' is distinguishable from 'Lapis' by the following characteristics:

1. 'Brilliant Blue' exhibits flowers that are darker blue in color than the flowers of 'Lapis'.
2. 'Brilliant Blue' exhibits a smaller overall height and width than 'Lapis'.
3. 'Brilliant Blue' exhibits peduncles that are shorter than the peduncles of 'Lapis'.
4. 'Brilliant Blue' exhibits pedicels that are shorter than the pedicels of 'Lapis'.

BRIEF DESCRIPTION OF THE DRAWING

The accompanying photograph illustrates the distinguishing traits of *Agapanthus* 'Brilliant Blue'. The plants in the photograph show an overall view of a 3 year old plant grown outdoors in Waitara, New Zealand. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Agapanthus* cultivar named 'Brilliant Blue'. Data was collected in Waitara, New Zealand from 3 year old outdoor grown plants. The time of year was Summer in the Southern Hemisphere and the temperature range was 18-25 degrees Centigrade during the day and 6-12 degrees Centigrade at night. The light level was natural outdoor light. Color determinations are in accordance with The Royal Horticultural Society Colour Chart 2001 edition, except where general color terms of ordinary dictionary significance are used. The growing requirements are similar to the species. 'Brilliant Blue' has not been tested under all possible conditions and phenotypic differences may be observed with variations in environmental, climatic, and cultural conditions, however, without any variance in genotype.

Botanical classification: *Agapanthus hybrida* 'Brilliant Blue'.

Use: Ornamental Perennial.

Parentage: 'Brilliant Blue' originated from open pollination of the female or seed parent plant *Agapanthus campanulatus* 'Lapis'.

Vigor: High.

Growth habit: Upright.

Plant shape: Basal leaves with central flowering scapes.

Overall height: Average 47.5 cm. in height.

Overall width: Average 37.5 cm. in width.

Low temperature tolerance: −5° Centigrade.

High temperature tolerance: 40° Centigrade.

Propagation: Tissue culture and division.

Crop time: 6 months to produce a finished liner plant.

Root system: Thick, fleshy, white-grey in color.

Foliage:

*Leaf arrangement*.—Basal.
*Compound or single*.—Single.
*Quantity of leaves per plant*.—Average 800.
*Texture*.—Smooth.
*Leaf shape*.—Linear.
*Leaf apex*.—Acute.
*Leaf base*.—Cuneate.
*Leaf length*.—Average 27 cm. in length.
*Leaf width*.—Average 11 mm. in width.
*Pubescence*.—Absent.
*Leaf margin*.—Entire.
*Young leaf color* (*lower surface*).—137C.
*Young leaf color* (*upper surface*).—137C.
*Mature leaf color* (*lower surface*).—137C.
*Mature leaf color* (*upper surface*).—137C.
*Vein color* (*under surface*).—137C.
*Vein color* (*upper surface*).—137C.
*Venation pattern*.—Parallel.
*Leaf attachment*.—Sessile.

Flower:

*Inflorescence arrangement*.—Campanulate flowers arranged in umbels on erect scapes.
*Natural flowering season*.—Summer.
*Fragrance*.—Slight scent.
*Inflorescence size*.—6 cm. in length and 10.5 cm. in width.
*Quantity of flowers per inflorescence*.—Average 64.
*Flower bud length*.—16 mm. in length.
*Flower bud diameter*.—5 mm. in diameter.
*Flower bud shape*.—Oblong.
*Bud color*.—93A.
*Flower aspect*.—Outward.
*Flower shape*.—Campanulate.
*Flower dimensions*.—27.5 mm. in diameter and 27.5 mm. in height.
*Flower longevity*.—Approximately 3 to 4 weeks
*Number of tepals*.—6.
*Fused or unfused*.—Lower 50% are fused.
*Tepal shape*.—Oblanceolate.
*Tepal margin*.—Entire.
*Tepal apex*.—Mucronate.
*Tepal base*.—Rounded.
*Tepal texture*.—Smooth.
*Tepal length*.—30 mm. in length.
*Tepal width*.—7 mm. in width.
*Tepal color when opening* (*upper side*).—94B, center stripe 89A.
*Tepal color when opening* (*under side*).—94B, center stripe 89A.
*Tepal color fully opened* (*upper side*).—94B, center stripe 89A.
*Tepal color fully opened* (*under side*).—94B, center stripe 89A.
*Tepal color fading to*.—Not fading.
*Self-cleaning or persistent*.—Persistent.

Peduncle:

*Peduncle dimensions*.—63.5 cm. in length and 5 mm. in diameter.
*Peduncle angle*.—35° from vertical.
*Peduncle color*.—138C.
*Peduncle strength*.—Strong.

Pedicels:

*Pedicel dimensions*.—29 mm. in length and 1.0 mm. in diameter.
*Pedicel color*.—138C.
*Pedicel strength*.—Moderate.

Reproduction organs:

*Stamen number*.—6.
*Anther shape*.—Oval.
*Anther size*.—2 mm.
*Anther color*.—187A.
*Amount of pollen*.—Low.
*Pollen color*.—187A.
*Pistil number*.—1.
*Pistil length*.—25 mm.
*Stigma shape*.—Trifid.
*Stigma color*.—155A.
*Style length*.—15 mm.
*Style color*.—94B.
*Ovary color*.—145C.

Fruit and seed:

*Fruit shape*.—Pod shaped, only 35% of pods contain seeds.
*Fruit dimensions*.—24 mm. in length and 11 mm. in width.
*Fruit color*.—136C.
*Seed dimensions*.—8 mm. in length and 2 mm. in width.
*Quantity of seeds*.—12 to 18 seeds per pod.
*Seed color*.—200A.

Disease and pest resistance: Plants of the new cultivar have not been observed for disease and pest resistance.

It is claimed:

1. A new and distinct variety of *Agapanthus* plant named 'Brilliant Blue' as described and illustrated.

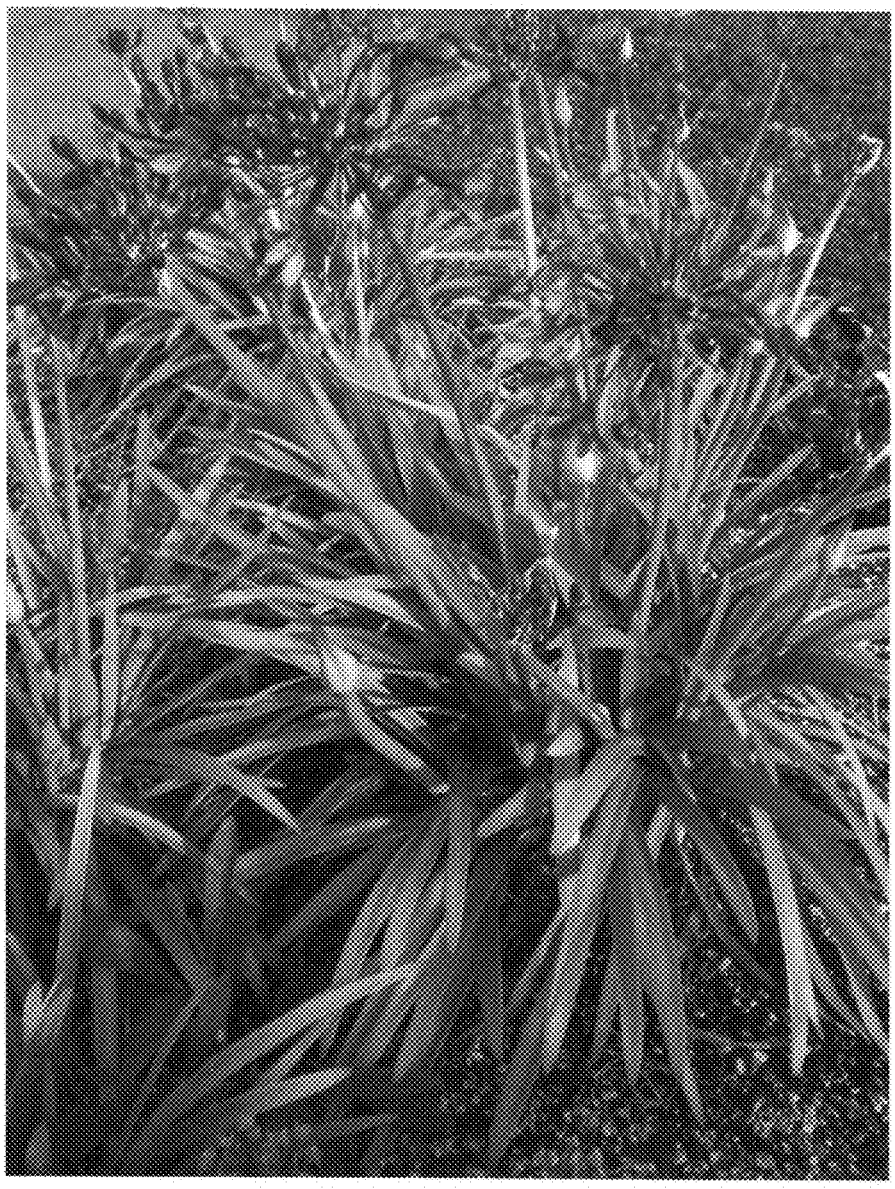

* * * * *